(12) United States Patent
Murray et al.

(10) Patent No.: US 8,900,242 B2
(45) Date of Patent: Dec. 2, 2014

(54) STYLUS ASSEMBLY

(75) Inventors: David Wycliffe Murray, Oxford (GB); Russell Lloyd, Wiltshire (GB)

(73) Assignee: Biomet UK Limited, Bridgend (GB)

( * ) Notice: Subject to any disclaimer, the term of this patent is extended or adjusted under 35 U.S.C. 154(b) by 226 days.

(21) Appl. No.: 13/545,510

(22) Filed: Jul. 10, 2012

(65) Prior Publication Data

US 2013/0012950 A1    Jan. 10, 2013

Related U.S. Application Data

(62) Division of application No. 11/920,464, filed as application No. PCT/GB2006/001777 on May 16, 2006, now Pat. No. 8,221,429.

(30) Foreign Application Priority Data

May 17, 2005   (GB) .................................. 0510058.1

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/15* | (2006.01) | |
| *A61B 17/00* | (2006.01) | |

(52) U.S. Cl.
CPC ......... *A61B 17/157* (2013.01); *A61B 17/00234* (2013.01)
USPC .......................................................... 606/88

(58) Field of Classification Search
CPC ..................................................... A61B 17/157
USPC .................................................................. 606/88
See application file for complete search history.

(56) References Cited

U.S. PATENT DOCUMENTS

| | | | |
|---|---|---|---|
| 5,683,396 A | 11/1997 | Tokish et al. | |
| 5,704,941 A | 1/1998 | Jacober et al. | |
| 6,290,704 B1 | 9/2001 | Burkinshaw et al. | |
| 8,221,429 B2 | 7/2012 | Murray et al. | |
| 2004/0249385 A1* | 12/2004 | Faoro | 606/88 |

FOREIGN PATENT DOCUMENTS

| | | |
|---|---|---|
| EP | 1470788 A1 | 10/2004 |
| WO | WO-2006123120 A1 | 11/2006 |

OTHER PUBLICATIONS

International Preliminary Report on Patentability for PCT/GB2006/001777 mailed on Nov. 29, 2007.

* cited by examiner

*Primary Examiner* — David Bates
(74) *Attorney, Agent, or Firm* — Harness, Dickey

(57) ABSTRACT

A stylus assembly is adapted to be attached to a surgical jig. The stylus assembly comprises a body having first and second arms with a space therebetween for receiving a portion of the surgical jig, a stylus adjustably mounted relative to the body, and a locking member in use, actuation of the locking member from an unlocked to a locked position enables locking of the body to the surgical jig and locking of the stylus relative to the body.

26 Claims, 2 Drawing Sheets

STYLUS ASSEMBLY

CROSS-REFERENCE TO RELATED APPLICATION

This application is a divisional of U.S. patent application Ser. No. 11/920,464 filed Apr. 3, 2008, which claims benefit of International Application No. PCT/GB2006/001777 filed May 16, 2006, which claims benefit of United Kingdom Application No. 0510058.1 filed May 17, 2005. The disclosures of these applications are incorporated by reference herein in their entirety.

FIELD

The present invention relates to a stylus assembly and particularly but not exclusively to a stylus assembly for use in positioning a guide used in the resection of a proximal human tibia.

BACKGROUND

This section provides background information related to the present disclosure which is not necessarily prior art.

It is known to provide a surgical jig having a cutting guide, which assists a surgeon in making accurate and repeatable cuts during surgery. The accuracy of a cut made using a cutting guide is mainly determined by the successful positioning and fastening of the cutting guide in the operative area. Typically, a stylus is attached to the cutting guide, which references from a reference point or marker on the body, for example, a bone. The stylus is either free to translate and/or rotate relative to the cutting guide, so that it may be adjusted, or is rigidly fixed to the cutting guide. An attachment mechanism mounts the stylus to the cutting guide, and a locking mechanism locks the stylus in a desired position relative to the attachment mechanism and hence the cutting guide. Once in the operating position, the jig can be attached to, for example, a bone using pins and/or bone screws.

The use of a stylus to position a cutting guide is common in joint replacement surgery. For example, during a total or partial knee replacement operation, it is necessary to resect the proximal tibia to a specific level. Existing tibial styli reference from the tibial plateau. This area of the joint is subject to considerable wear and, in a knee requiring joint replacement is likely to be damaged. Therefore, the tibial plateau does not provide a reliable reference position. It is desirable to provide a stylus assembly that enables referencing from an area of undamaged bone, which would provide a more reliable reference position.

Once a stylus has been used to position a cutting guide, the stylus is usually removed, in order to increase the working space available to the surgeon. A problem of existing arrangements is that the removal of the stylus can cause unintentional and unnoticed movement of the cutting guide. This leads to inaccurate positioning of the cutting guide, with the result that the surgeons' incisions are misdirected. It is therefore also desirable to provide a stylus assembly which can be removed with the minimum of handling.

SUMMARY OF INVENTION

This section provides a general summary of the disclosure, and is not a comprehensive disclosure of its full scope or all of its features.

According to the present invention there is provided a stylus assembly adapted to be attached to a surgical jig, the stylus assembly comprising a body having first and second arms with a space therebetween for receiving a portion of the surgical jig, a stylus adjustably mounted relative to the body, and a locking member. In use, actuation of the locking member from an unlocked to a locked position locks the body to the surgical jig and locks the stylus relative to the body.

It is an advantage of the invention that the stylus assembly can be locked onto a surgical jig and the stylus adjusted and locked into position by operation of a single locking member.

In particular, when resecting a proximal tibia, the stylus assembly of the invention can advantageously be positioned on a surgical jig and the stylus loosely inserted into the wound of a patient. Only when finally positioned does the locking member have to be actuated. The loose insertion of the stylus enables the stylus to reference from the posterior femoral condyle with the knee in flexion. The posterior femoral condyle is not subject to as much wear as the anterior femoral condyle. The surgical jig can therefore be positioned more accurately than with existing stylus assemblies, which reference from the anterior femoral condyle.

A retaining member may extend outwardly from the first arm of the body with an enlarged retaining head at its distal end.

The stylus may have a slotted central portion, which may be mounted about the retaining member, thereby enabling translational and rotational movement of the stylus relative to the body.

A bifurcated locking element having first and second arms may be mounted about the retaining member.

An aperture may be provided through the first arm of the locking element.

A portion of the first arm of the locking element may be positioned between the body and the stylus with the retaining member passing through the aperture.

The second arm of the locking element may extend into the space between the first and second arms of the body.

A portion of the first arm of the body may be located in a space between the first and second bifurcated arms of the locking element.

A first clearance may be provided between the second arm of the locking element and the portion of the first arm of the body located in the space between the first and second arms of the locking element.

A second clearance may be provided between an underside of the retaining head of the retaining member and the slotted portion of the stylus.

The first clearance may be greater than the second clearance, thereby allowing movement of the retaining element towards the distal end of the retaining member until the stylus is clamped between the underside of the enlarged retaining head and first arm of the locking element.

The locking member may be a cam.

The cam may be eccentrically pivotally mounted to the second arm of the body.

A cam lever may be attached to the cam, to enable rotation of the cam.

A channel may be provided in the body for receiving the cam lever with a snug fit when the locking member is in an unlocked position.

An end portion of the cam lever may extend out of the channel when the lever is in the unlocked position.

The cam may extend into the space between the first and second arms of the body, when the locking member is moved from an unlocked to a locked position.

The cam lever advantageously enables the cam to be actuated smoothly, without backlash. Furthermore, the locking surface of the cam may move a very small distance, typically 1 mm, and therefore the cam can be actuated without affecting the position of the stylus, once positioned. There is also no build up of tolerances, as with conventional stylus assemblies, which are adjusted by means of, for example, screw threads.

The body may be provided with a stop between the first and second arms, which locates against an edge of the portion of the surgical jig positioned between the first and second arms.

The stylus assembly may be made from stainless steel, or any other suitable metal, metal alloy or plastics.

The stylus assembly may be provided in various sizes, but may be typically 10 mm wide.

The stylus assembly has the advantage of being "slimline" in comparison with other assemblies, and may be most suitably used in minimally invasive surgery, in which the size of the operative wound is kept to a minimum, in order to reduce the risk of infection and reduce patient recovery time.

According to a further aspect of the invention there is provided a method of positioning a surgical jig using a stylus assembly, the stylus assembly comprising a body having first and second arms with a space therebetween, a stylus adjustably mounted relative to the body, and a locking member, the method comprising the steps of positioning the stylus assembly with a portion of the surgical jig in the space between the first and second arms, adjusting the stylus to reference from a desired reference position, and actuating the locking member from an unlocked to a locked position to lock the body of the stylus assembly to the surgical jig and to lock the stylus relative to the body.

The stylus may reference off a posterior femoral condyle.

The surgical jig may be adapted to guide a proximal tibial resection.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION OF THE DRAWINGS

Example embodiments will now be described more fully with reference to the accompanying drawings.

Figure 1:
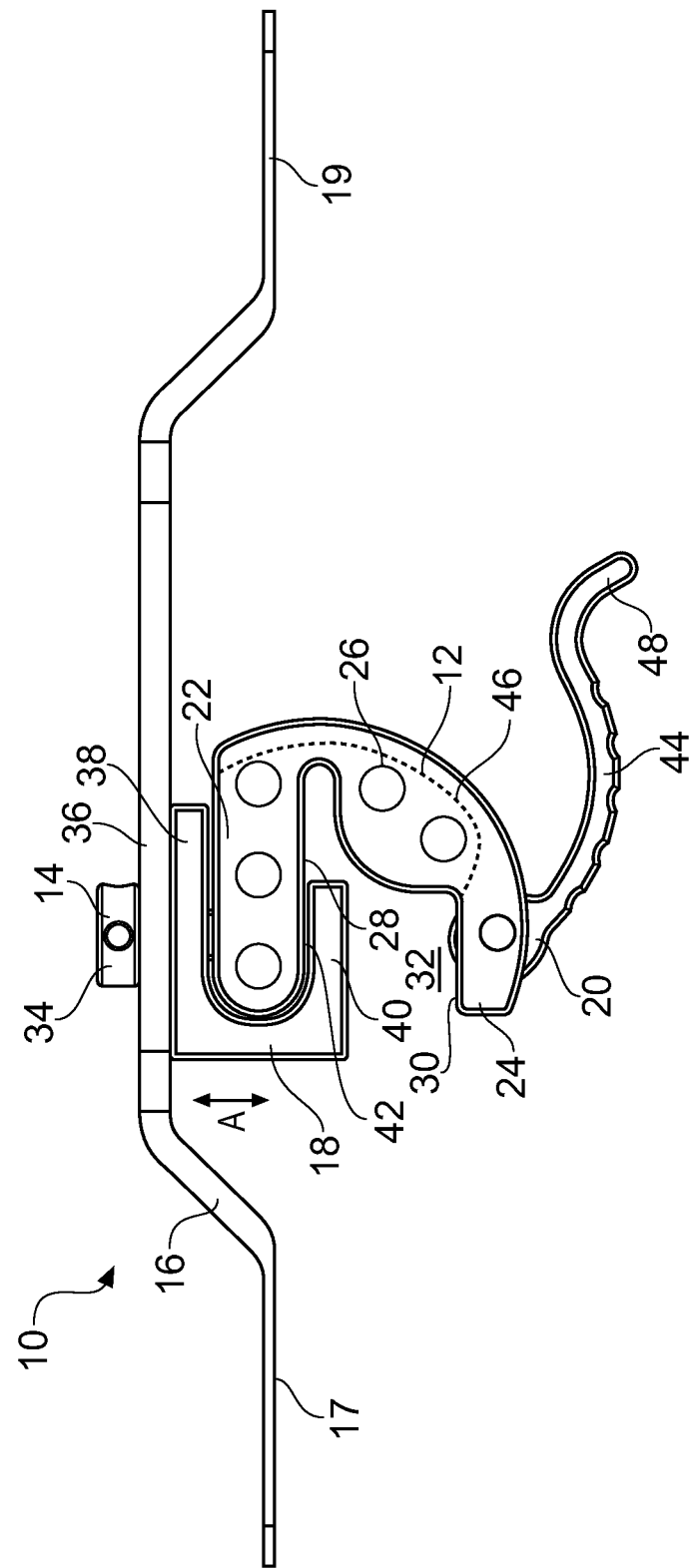
FIG. 1 shows a side view of a stylus assembly in accordance with the invention.

Referring firstly to FIG. 1, a stylus assembly is indicated generally at 10. The stylus assembly 10 comprises a substantially C-shaped body 12, a retaining member 14 attached to the body 10, a stylus 16, mounted about and retained by the retaining member 14, a locking element 18 for locking the position of the stylus 14, and a locking member 20, for securing the stylus assembly to a surgical guide, for example, a resection guide.

The C-shaped body 12 has a first arm 22, which is the upper arm as viewed, a lower arm 24 and a central portion 26 connecting the upper and lower arms 22,24 together. The inner surfaces 28, 30 of the arms 22,24, ie the surfaces facing one another, have a space 32 therebetween for receiving part of a surgical guide, to which the stylus assembly is to be attached.

The retaining member 14 is a pin or screw, which extends outwardly from the first arm 22 of the body 12 and has an enlarged head 34. The pin 14 extends in a direction away from that of the lower arm 24, ie vertically as viewed in FIG. 1. The stylus 16 has a central portion 36 with a longitudinal slot running therethrough. The pin 14 is located within the slot as a clearance fit, thus enabling translation and rotation of the stylus 16 about the pin 14. The stylus is restrained on the pin by virtue of the enlarged head 34.

The ends of the stylus, indicated at 17 and 19, are cranked downwards from the central portion 36 by different distances, in order to provide lateral reference surfaces at different heights, relative to the body 12 of the stylus assembly 10.

The locking element 18 is bifurcated and has first and second arms 38, 40, which are disposed one either side of the first arm 22 of the body 12. An aperture is provided through the first arm 38 of the locking element 18, through which the retaining pin 14 passes. The stylus 16 is disposed above the first arm 38 of the locking element (as viewed) between the locking element and enlarged head 34. The upper surface of the first arm 38 provides a surface, over which the stylus 16 is able to translate and rotate.

The second arm 40 of the locking element extends into the space 32 between the first and second arms 22, 24 of the body 12. In other words, the first arm 22 of the body 12 and the second arm 40 of the locking element 18 wrap around one another.

Figure 2:
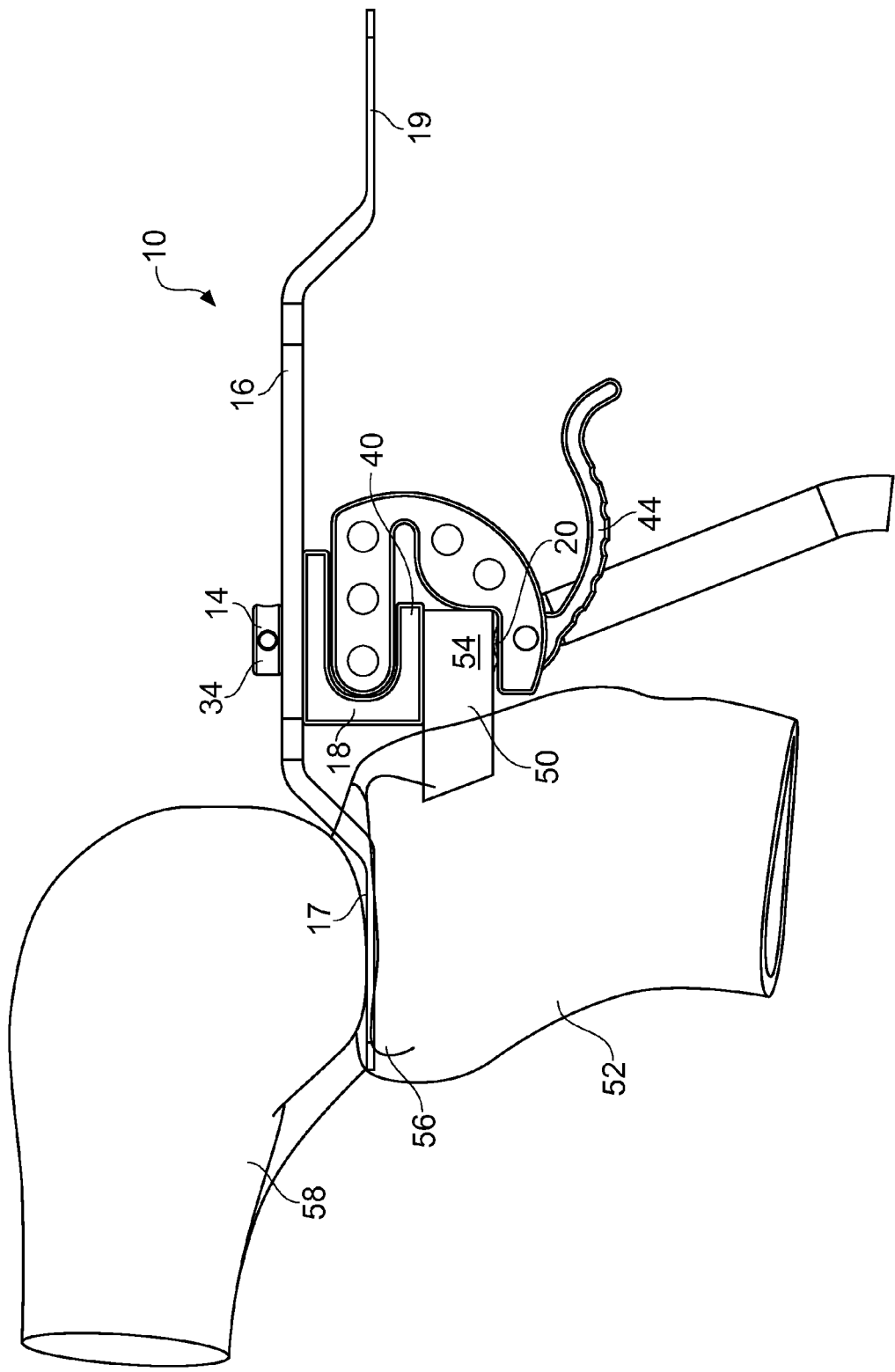
FIG. 2 shows a side view of the stylus assembly of FIG. 1 in use, secured to a resection guide.

The locking element 18 is able to move a short distance vertically as indicated by arrow A, relative to the body 12. A first clearance distance, indicated partly at 42, is provided between the upper surface of the second arm 40 of the locking element and the lower surface of the first arm 22 of the body 12. A second clearance distance (not shown in the Figs) is provided between the underside of the head 34 and the upper surface of the central portion 36 of the stylus 16. The first clearance 42 is greater than the second clearance, thereby allowing movement of the locking element 18 towards the head 34 until the stylus 16 is clamped between the underside of the head 34 and the first arm 38 of the locking element 18 as shown in FIGS. 1 and 2.

The locking member 20 is a cam, which is eccentrically pivotally mounted to the second arm 24 of the body 12. A cam lever 44 is integrally formed with the cam, which extends into the space 32 between the first and second arms 22, 24 of the body 12, when actuated to a locked position as shown in FIGS. 1 and 2.

A slot or channel 46, shown in dotted outline in FIG. 1, is provided in the rear edge of the body 12, which receives the cam lever 44 with a snug fit when the lever is in a stowed position. An end portion 48 of the cam lever 44 extends out of the channel 46 by which the lever can easily be rotated using a thumb and index finger.

The central portion 26 of the body 12 has an inner surface, between the arms 22, 24, which acts as a stop, against which a surgical jig can rest. The stylus assembly 10 can be made from stainless steel, metal alloy or any suitable plastics.

Referring now to FIG. 2, in use, the stylus assembly 10 is used to position a surgical jig 50 including a cutting guide. In FIG. 2, the jig 50 is shown attached to a patient's tibia 52, by means of, for example, pins or bone screws, for performing a resection of the proximal tibia in a knee operation. Prior to fixing the jig 50, a portion 54 of the jig is positioned in the space 32 of the stylus assembly 10. The stylus 16 is then adjusted about the retaining member 14 until one of the ends 17, 18 is located against the posterior femoral condyle 56, which provides a reference surface of relatively unworn bone. The looseness or mobility of the stylus assembly 10 facilitates the positioning of the stylus 16 between the tibia 52 and femur 58 through the operative wound. The surgeon can choose which end 17, 19 of the stylus to use as a reference surface, the different heights of the ends of the stylus providing for two different levels of resection.

Once in position, the cam lever 44 is rotated to the locked position (as shown), which causes the cam 20 to extend into the space 32. This clamps the jig 50 between the cam 20 and the second arm 40 of the locking element 18. In so doing, the locking element is forced upwards, as viewed, towards the head 44 of the retaining member 14, and the first arm 38 of the locking element 18 clamps the stylus 16 against the enlarged head 34.

The actuation of the cam 20 is smooth, and the position of the stylus and jig can be maintained with ease relative to the tibia 52. Removal of the stylus assembly from the jig 50 is effected by rotating the cam lever 44 to its stored position, which causes the cam to retract into the channel 46 of the body 12.

The stylus assembly 10 and jig 50 are compatible with one another, if the portion 54 of the jig 50, which is received in the space 32 of the body 12, is a clearance fit in this space. This is because the axial movement of the cam 20 into the space 32 is kept to a minimum, for example 1 mm, in order to ensure that movement of the stylus 16 is kept to an absolute minimum, eg 0.25 mm. If the portion 54 of the jig 50 is too small to substantially fill the space 32 then the locking element 18 may not be sufficiently displaced to lock the stylus 16. This being the case, it is possible to increase the thickness of the portion 54 of the jig 50, by means of one or more shims (not shown).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of positioning a surgical jig using a stylus assembly, the stylus assembly comprising a body having first and second arms with a space therebetween, a stylus adjustably mounted relative to the body, locking member, a first locking arm between the first arm and the stylus, and a second locking arm between the first arm and the surgical jig, the method comprising:
    positioning the stylus assembly with a portion of the surgical jig in the space between the first and the second arms;
    adjusting the stylus to reference from a desired reference position; and
    actuating the locking member from an unlocked to a locked position to lock the body of the stylus assembly to the surgical jig between the second locking arm and the second arm and to lock the stylus relative to the body.

2. The method of claim 1, further comprising referencing the stylus relative to a posterior femoral condyle.

3. The method of claim 1, further comprising guiding a proximal tibial resection with the surgical jig.

4. The method of claim 1, further comprising referencing an end of the stylus off a posterior femoral condyle.

5. The method of claim 1, further comprising pivoting a cam lever of the locking member to extend a cam of the locking member further into the space between the first and the second arms of the body.

6. The method of claim 1, further comprising pivoting a cam lever of the locking member to extend a cam of the locking member further into the space between the first and the second arms of the body, the cam integrally formed with the cam lever.

7. A method of positioning a surgical jig using a stylus assembly comprising:
    positioning the stylus assembly relative to a bone, the stylus assembly including the surgical jig between a first body arm and a second body arm of a body of the stylus assembly, the first body arm is mounted to a stylus of the stylus assembly with a retaining member, a first locking arm of a locking element is between the first body arm and the stylus, a second locking arm of the locking element is between the first body arm and the surgical jig, the retaining member extends through an aperture defined by the first locking arm;
    adjusting the stylus to reference from a reference position on the bone; and
    actuating a locking member from an unlocked to a locked position to lock the body of the stylus assembly to the surgical jig and to lock the stylus relative to the body.

8. The method of claim 7, further comprising referencing the stylus relative to a posterior femoral condyle.

9. The method of claim 7, further comprising guiding a proximal tibial resection with the surgical jig.

10. The method of claim 7, further comprising referencing an end of the stylus off a posterior femoral condyle.

11. The method of claim 7, further comprising pivoting a cam lever of the locking member to extend a cam of the locking member further into a space defined between the first and the second arms of the body.

12. The method of claim 7, further comprising pivoting a cam lever of the locking member to extend a cam of the locking member further into a space defined between the first and the second arms of the body, the cam integrally formed with the cam lever.

13. The method of claim 7, wherein actuating the locking member includes pivoting a cam lever mounted to the second body arm.

14. The method of claim 7, wherein actuating the locking member includes pivoting a cam lever eccentrically pivotally mounted to the body.

15. A method of positioning a surgical jig using a stylus assembly comprising:
    positioning the stylus assembly relative a bone, the stylus assembly including the surgical jig between a first body arm and a second body arm of a body of the stylus assembly;
    adjusting a stylus of the stylus assembly to reference from a reference position on the bone, the stylus is mounted to the first body arm with a retaining member extending from the first body arm through an aperture defined in a first locking arm of a locking element, the first body arm is between the first locking arm and a second locking arm of the locking element; and
    actuating a locking member mounted to the body to clamp the surgical jig between the second locking arm and the second body arm, and force the locking element toward a head of the retaining member such that the first locking arm clamps the stylus against the head.

16. The method of claim 15, further comprising referencing the stylus relative to a posterior femoral condyle.

17. The method of claim 15, further comprising guiding a proximal tibial resection with the surgical jig.

18. The method of claim 15, further comprising referencing an end of the stylus off a posterior femoral condyle.

19. The method of claim 15, wherein actuating the locking member includes pivoting a cam lever of the locking member to extend a cam of the locking member further from the second body arm.

20. The method of claim 15, wherein actuating the locking member includes pivoting a cam lever of the locking member to extend a cam of the locking member further from the second body arm, the cam integrally formed with the cam lever.

21. A method of clamping a surgical jig with a stylus assembly, the stylus assembly comprising a body having first and second arms, a stylus adjustably mounted relative to the body, a locking member acting between the body and the stylus, a first locking arm between the first arm and the stylus, and a second locking arm between the first arm and the surgical jig, the method comprising the successive steps of:

adjusting the stylus relative to the body to reference from a desired reference position and positioning the surgical jig relative to the body, with the locking member in an unlocked position; and actuating the locking member from an unlocked to a locked position to clamp the body of the stylus assembly to the surgical jig between the second locking arm and the second arm and to simultaneously clamp the stylus relative to the body.

22. The method of claim 21, further comprising referencing the stylus relative to a posterior femoral condyle.

23. The method of claim 21, further comprising guiding a proximal tibial resection with the surgical jig.

24. The method of claim 21, further comprising referencing an end of the stylus off a posterior femoral condyle.

25. The method of claim 21, further comprising pivoting a cam lever of the locking member to extend a cam of the locking member further into a space between first and second arms of the body.

26. The method of claim 21, further comprising pivoting a cam lever of the locking member to extend a cam of the locking member further into a space between first and second arms of the body, the cam integrally formed with the cam lever.

* * * * *

UNITED STATES PATENT AND TRADEMARK OFFICE
CERTIFICATE OF CORRECTION

PATENT NO. : 8,900,242 B2
APPLICATION NO. : 13/545510
DATED : December 2, 2014
INVENTOR(S) : David Wycliffe Murray et al.

It is certified that error appears in the above-identified patent and that said Letters Patent is hereby corrected as shown below:

In the Specification,

Column 3, Line 61; Delete "14," and insert --16,--.

Column 5, Line 14; Delete "44" and insert --34--.

Signed and Sealed this
Twelfth Day of May, 2015

Michelle K. Lee
*Director of the United States Patent and Trademark Office*